US010201475B2

(12) United States Patent
Jöbstl et al.

(10) Patent No.: US 10,201,475 B2
(45) Date of Patent: Feb. 12, 2019

(54) CONTAINER CLOSURE SYSTEM

(71) Applicant: Fresenius Kabi Deutschland GmbH, Bad Homburg (DE)

(72) Inventors: Elisabeth Jöbstl, Vasoldsberg (AT); Gerald Wegner, Bad Nauheim-Steinfurth (DE); Asbjørn Solberg-Eriksen, Halden (NO); Eric Delaporte, Huest (FR)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 14/819,356

(22) Filed: Aug. 5, 2015

(65) Prior Publication Data

US 2016/0213566 A1 Jul. 28, 2016

(30) Foreign Application Priority Data

Jan. 26, 2015 (EP) .................................... 15152521

(51) Int. Cl.
*A61B 50/00* (2016.01)
*A61J 1/14* (2006.01)
(Continued)

(52) U.S. Cl.
CPC ............... *A61J 1/1468* (2015.05); *A61J 1/16* (2013.01); *B65D 25/205* (2013.01); *B65D 31/02* (2013.01);
(Continued)

(58) Field of Classification Search
CPC . A61J 1/1468; A61J 1/10; A61J 1/165; B65D 25/205; B65D 77/04; B65D 33/004; B65D 77/044; B65D 77/00
(Continued)

(56) References Cited

U.S. PATENT DOCUMENTS 4,322,465 A * 3/1982 Webster .................. B32B 27/32 206/484

(Continued)

FOREIGN PATENT DOCUMENTS

GB 2 342 912 A 4/2000
WO WO 2010/052844 A1 5/2010

OTHER PUBLICATIONS

European Patent Office, Extended European Search Report in European Patent Application No. 15152521.9 (dated Mar. 10, 2015).

*Primary Examiner* — Jacob K Ackun
*Assistant Examiner* — Jenine Pagan
(74) *Attorney, Agent, or Firm* — Leydig, Voit & Mayer, Ltd.

(57) ABSTRACT

The invention relates to a pharmaceutical product or container closure system containing an overpouch with an intransparent first foil and a transparent second foil, a transparent primary container for holding a transparent liquid, e.g., a pharmaceutical formulation, wherein the transparent primary container is packed within the overpouch and labeled with at least one label and wherein the at least one label acts as a light absorbing segment having a reflection $R_L$ for light in the range of about 350 nm to about 800 nm and an inner surface of the intransparent first foil of the overpouch acts as a light reflecting background having a reflection $R_F$ for light in the direction of the primary container in the range of about 350 nm to about 800 nm with $R_F \neq R_L$. By the transparent second foil and the inventive reflection properties it is achieved that the at least one label on the primary container is visible and readable. Additionally, visual inspection of the content of the transparent primary container is possible. A good contrast is achieved to enhance machine and human readability.

25 Claims, 3 Drawing Sheets

(51) Int. Cl.

*B65D 30/08* (2006.01)
*B65D 33/00* (2006.01)
*B65D 77/04* (2006.01)
*B65D 25/20* (2006.01)
*A61J 1/16* (2006.01)
*A61J 1/10* (2006.01)

(52) U.S. Cl.

CPC ........... *B65D 33/004* (2013.01); *B65D 77/04* (2013.01); *A61J 1/10* (2013.01); *B65D 2203/02* (2013.01); *B65D 2203/06* (2013.01)

(58) Field of Classification Search

USPC ............ 206/438, 524.1, 524.3, 524.2, 524.6, 206/524.7, 484, 484.1, 484.2; 383/106, 383/116, 109, 113; 604/408, 410, 403, 604/415

See application file for complete search history.

(56) References Cited

U.S. PATENT DOCUMENTS 4,467,588 A * 8/1984 Carveth ................ A61J 1/2093 206/219
5,763,028 A * 6/1998 Matsumoto ............... A61L 2/04 206/484.2
6,241,717 B1 * 6/2001 Niedospial, Jr. .......... A61J 1/10 206/828
6,613,036 B1 * 9/2003 Farmer ..................... A61J 1/10 206/438
7,025,877 B1 * 4/2006 de Gheldere ............. A61J 1/10 210/202
7,213,760 B2 * 5/2007 Mase ..................... G06K 1/126 235/462.01
7,307,245 B2 * 12/2007 Faries, Jr. ............. A61J 1/1475 165/254
2003/0072676 A1 * 4/2003 Fletcher-Haynes ....... A61J 1/10 422/23
2003/0209453 A1 * 11/2003 Herman .............. A61M 15/009 206/204
2004/0188281 A1 9/2004 Masanobu et al.
2008/0065043 A1 * 3/2008 Bemer ...................... A61J 1/10 604/408
2012/0124943 A1 * 5/2012 Nakamura ................ A61L 2/26 53/425
2012/0145580 A1 * 6/2012 Paruit ....................... A61J 1/10 206/459.5
2013/0289496 A1 * 10/2013 Langan ............... A61M 5/1417 604/257
2013/0327677 A1 12/2013 McDorman
2015/0069056 A1 * 3/2015 Kishimoto ............. B65D 77/04 220/23.87

* cited by examiner

CONTAINER CLOSURE SYSTEM

CROSS-REFERENCE TO RELATED APPLICATIONS

This application claims the benefit of European patent application no. 15152521.9, filed Jan. 26, 2015, the contents of which is incorporated herein by reference in its entirety.

BACKGROUND OF THE INVENTION

Pharmaceutical solutions in containers and bags, respectively, often contain oxygen sensitive ingredients. As such a container it is usually used a primary bag which is fully transparent to allow visual inspection of the pharmaceutical solution in the primary bag. The primary bag usually could be made out of a multi-layer film and could have good chemical resistance, good welding characteristics and could be heat sterilisable. One or two tubes could be put in place by a heat welding process and serve to connect one or two ports to the multi-layer film. One port can be used for the infusion of the content of the primary bag into a patient. A second port can be used to inject additional compatible solutions into the content of the primary bag. Furthermore, labeling information is usually printed directly on the primary bag.

Such primary bags are often overwrapped by an overpouch, preferably immediately after filling and under reduced pressure or vacuum. Usually a secondary bag is used as such an overpouch. This outer secondary bag prevents largely gas permeation into the primary bag and serves therefore as a protection of the content of the primary bag against oxygen and water vapor transmission as well as against other environmental influences. Labels and/or barcodes are often provided on the secondary bag as well.

It is current praxis to use an aluminium overpouch as a secondary bag to provide a barrier for oxygen and water vapor. With a container closure system with such a secondary bag as an overpouch a visual inspection of the content of the primary bag is not possible. Furthermore, the label printed on the primary bag is covered by the intransparent overpouch. Thus, the label has to be reprinted on the overwrap because it is vital to have all necessary product information readily available without opening the overpouch.

It is therefore an object of the invention to provide an improved container closure system, in particular which makes a reprinting of the label of the primary bag onto the overpouch redundant. Another object of the invention is to allow or to improve visual inspection of the label and of the content of a transparent primary container of such a container closure system.

SUMMARY OF THE INVENTION

The invention concerns a pharmaceutical product or container closure system with a container which is filled with a liquid and with an overpouch in which the container is packed.

The inventive pharmaceutical product or container closure system comprises the following components: An overpouch with an intransparent first foil and a transparent second foil and a transparent primary container, preferably embodied as a bag, for holding or storing a liquid, such as a pharmaceutical formulation. The transparent primary container is packed or encased within the overpouch and labeled with at least one label. The label has a reflection for light ($R_L$) and an inner surface of the intransparent first foil of the overpouch has a reflection for light ($R_F$) in the direction of the primary container, and the label can be read by a human or by a machine, e.g., a barcode scanner.

According to a first alternative of the invention the at least one label acts as a light absorbing segment having a reflection $R_L$ for light in the range of about 350 nm to about 800 nm and an inner surface of the intransparent first foil of the overpouch acts as a light reflecting background having a reflection $R_F$ for light in the direction of the primary container in the range of about 350 nm to about 800 nm with $R_F>R_L$. In another embodiment of this alternative, the at least one label acts as a light absorbing segment having a reflection $R_L$ for light in the range of 350 nm to 800 nm and an inner surface of the intransparent first foil of the overpouch acts as a light reflecting background having a reflection $R_F$ for light in the direction of the primary container in the range of 350 nm to 800 nm with $R_F>R_L$.

According to a second alternative of the invention the at least one label acts as a light reflecting segment having a reflection $R_L$ for light in the range of about 350 nm to about 800 nm and an inner surface of the intransparent first foil of the overpouch acts as a light absorbing background having a reflection $R_F$ for light in the direction of the primary container in the range of about 350 nm to about 800 nm with $R_L>R_F$. In another embodiment of this alternative, the at least one label acts as a light reflecting segment having a reflection $R_L$ for light in the range of 350 nm to 800 nm and an inner surface of the intransparent first foil of the overpouch acts as a light absorbing background having a reflection $R_F$ for light in the direction of the primary container in the range of 350 nm to 800 nm with $R_L>R_F$.

By means of the transparent second foil and the inventive reflection properties wherein $R_L \neq R_F$ it is achieved that the at least one label on the primary container is still visible and readable. Additionally, visual inspection of the content of the transparent primary container is possible. In particular by the inventive reflection properties a good contrast is achieved to enhance machine and human readability of the label.

With this inventive pharmaceutical product or container closure system design it is possible to overwrap a primary container which holds a liquid, e.g., a pharmaceutical formulation without covering labels which are arranged, especially printed, on the primary container. The primary container is filled with the liquid, such as a pharmaceutical formulation. The inventive pharmaceutical product or container closure system is especially suitable for transparent liquids and pharmaceutical formulations. It is mentioned that under the term pharmaceutical formulation not only liquid pharmaceutical formulations are meant but also solutions for infusion, nutrition and/or dialysis. This enumeration is exemplary only and not restricted to mentioned examples.

The pharmaceutical formulation can be a liquid or a mixture of liquids. In certain embodiments, the pharmaceutical formulation is a solution, a suspension, or an emulsion. In some embodiments, the pharmaceutical formulation comprises at least one compound and at least one liquid. The compound can be fully dissolved in the liquid, partially dissolved in the liquid, or suspended in the liquid. Alternatively, or additionally, the pharmaceutical formulation can be a powder, such as a lyophilized powder, comprising at least one compound.

The compound of the pharmaceutical formulation can be a therapeutic agent, a diagnostic agent, a nutrient, or a combination thereof. Examples of therapeutic agents include, but are not limited to antiinfectives, anesthetics, analgesics, anticoagulants, chemotherapeutics, hormones, antihypertensives, antiinflammatories, antiemetics, bronchodilators, adrenergics, immunoglobulins, antipsychotics, antidepressants, and combinations thereof. Examples of diagnostic agents, include, but are not limited to x-ray, MRI and ultrasound contrast agents, cholecystokinetics, vasodilators, and combinations thereof. Examples of nutrients include, but are not limited to, salts, carbohydrates, minerals, vitamins, lipids, and combinations thereof.

In some embodiments, the pharmaceutical formulation comprises moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, ropivacaine, lidocaine, propofol, decitabine, azacitidine, docetaxel, pemetrexed, palonosetron, aprepitant, fosaprepitant, famotidine, amiodarone, nitroglycerin, nicardipine, clevidipine, dobutamine, magnesium sulfate, sodium chloride, potassium chloride, lactated ringer's, dextrose, mannitol, or a combination thereof.

The pharmaceutical formulation can contain one or more excipients. Non-limiting examples of excipients include carriers, diluents, salts, buffers, stabilizers, solubilizers, preservatives, chelating agents, antioxidants, and tonicity contributors. Excipients that may be useful in preparing pharmaceutical formulations, suitable concentration ranges, and methods of preparing such formulations, are described, for example, in Remington, J. P. et al. (2006). *Remington: The Science and Practice of Pharmacy*. Philadelphia: Lippincott Williams & Wilkins; and in Rowe, R. C. et al. (2012). *Handbook of Pharmaceutical Excipients*. London: Pharmaceutical Press.

Preferably the entire area of the second foil is transparent and/or the entire area of the primary container is transparent. In case the area of the second foil is only partially transparent, the transparent area preferably comprises an area which is located above or covers the area of the primary container in which the label is located. Preferably the entire area of the first foil is intransparent. In case the area of the first foil is only partially intransparent, the intransparent area preferably comprises at least an area which is located below or covered by the area of the primary container in which the label is located.

Subsequently light is described as electromagnetic radiation as well. By the transparent second preferably multilayer foil and the inventive reflection properties for electromagnetic radiation in the visible range of electromagnetic radiation between 350 nm to 800 nm of the foils of the overpouch and the primary container it is achieved that the labels on the primary container are still visible and are readable by machines.

In a first embodiment of the first alternative of the invention the label is provided by a dark color and the inner surface of the intransparent first foil of the overpouch is provided by a light color. In a first embodiment of the second alternative of the invention the label is provided by a light color and the inner surface of the intransparent first foil of the overpouch is provided by a dark color. An enhanced contrast and therefore an enhanced readability are achieved. In some embodiments, the light color is white. In other embodiments, the light color is a variation, shade, or tint of white, e.g., off-white, cream, eggshell, ivory, bone, cornsilk, linen, beige, or light gray. In yet other embodiments, the light color is a tint of pink, red, brown, orange, yellow, green, cyan, blue, or violet. In some embodiments, the dark color is black. In other embodiments, the dark color is a variation, shade, or tint of black, e.g., onyx, charcoal, ebony, jet, olive, or dark gray. In yet other embodiments, the dark color is a shade of pink, red, brown, orange, yellow, green, cyan, blue, or violet.

In a further embodiment of the first and the second alternative of the invention the label is imprinted on the outer side of the transparent primary container, preferably on the outer side of the transparent primary container facing the transparent second foil of the overpouch. Labels and/or barcodes could be printed on the primary bag using the hot stamp printing technique. In this technique the ink is transferred from a carrier foil and melted to the surface of the bag during a short heating. This technique results in a print that is glossy and rub resistant and is even autoclavable.

In a further embodiment of the first and the second alternative of the invention the inner surface of the intransparent first foil of the overpouch is provided by a colored polymeric layer. Preferably the polymeric layer is made of or comprises polypropylene. In a preferred embodiment the color is part of the polymeric layer. The color belongs to the bulk. I.e. the color is a component of the blend to produce the polymer. The corresponding color can be provided by pigments and/or by dies. Preferably the color is not provided by an additional colored coating or painting on the polymeric layer surface.

The pharmaceutical product or container closure system is characterized in a further embodiment such that the at least one label contains text information, a barcode, a data matrix, a symbol and/or a drawing. Preferably it is or they are related to the content and/or the use of the primary container. The enumeration is exemplary and not restricted to the mentioned examples. The barcode can be a 1-dimensional or 2-dimensional barcode.

The inventive pharmaceutical product or container closure system is characterised in one embodiment of the first or the second inventive alternative by the following reflection parameters: a) $0.5\times R_F \geq R_L$ and $R_F \geq 0.5$ or b) $0.5\times R_L \geq 0.5$. Contrast and therefore human or machine readability are enhanced.

In the case that the reflection $R_F$ of the intransparent foil of the overpouch in the visible range of electromagnetic radiation between 350 nm to 800 nm is at least 0.5 and at least twice as high as the reflection $R_L$ of the at least one label on the primary container a good contrast of the at least one label of the primary container on the background of the intransparent foil of the overpouch is given. In the case that the reflection $R_L$ of the at least one label on the primary container in the visible range of electromagnetic radiation between 350 nm to 800 nm is at least 0.5 and at least twice as high as the reflection $R_F$ of the intransparent foil of the overpouch a good contrast of the at least one label of the primary container on the background of the intransparent foil of the overpouch is given as well.

The difference of the reflected radiation in the visible range of electromagnetic radiation between 350 nm to 800 nm gives a good contrast of the at least one label of the primary container on the background of the intransparent foil of the overpouch. Therefore it is ensured that human beings can read the at least one label as well as label reader machines while the primary container is still packed in the overpouch. It is neither necessary to open the overpouch nor to reprint the at least one label on the overpouch to get the information of the label. The primary container with the pharmaceutical solution is safely packed into the overpouch and the information of the at least one label of the primary container is accessible at any time without opening the overpouch. Furthermore a visible inspection of the pharmaceutical solution within the primary container is possible by the inventive pharmaceutical product or container closure system without opening the overpouch. The reflection of the transparent foils can be near zero and can therefore be neglected even if the radiation reflected by intransparent foil of the overpouch is running twice through it.

To get an even better contrast of the at least one label of the primary container on the background of the intransparent foil of the overpouch a symbol contrast is defined by the absolute value of the difference between the reflection $R_F$ of the intransparent foil of the overpouch and the reflection $R_L$ of the at least one label of the primary container in the visible range of electromagnetic radiation between 350 nm to 800 nm wherein this symbol contrast SC is specified by $SC=|R_F-R_L|\geq 0.5$. This feature of the reflection properties of the intransparent foil of the overpouch and the at least one label ensures a good machine readability without making too high and cost intensive demands on the optics of the machine which has to read the label. Preferably the parameters RL, RF and SC are determined according to test standard ISO/IEC15416.

Regarding a further embodiment of the inventive pharmaceutical product or container closure system the reflection properties $R_F$ and $R_L$ of the intransparent foil of the overpouch and the label of the primary container in the visible range of electromagnetic radiation between 350 nm to 800 nm are specified as follows:

c) $R_F\geq 0.75$, preferred $R_F\geq 0.85$, especially preferred $R_F\geq 0.9$, and $R_L\leq 0.25$, preferred $R_L\leq 0.15$, especially preferred $R_L\leq 0.1$ or d) $R_L\geq 0.75$, preferred $R_L\geq 0.85$, especially preferred $R_L\geq 0.9$, and $R_F\leq 0.25$, preferred $R_F\leq 0.15$, especially preferred $R_F\leq 0.1$.

These features ensure even a better machine readability since the contrast of the at least one label of the primary container on the background of the intransparent foil of the overpouch is furthermore increased.

The overpouch is a container or overpack for holding the primary container. The overpouch can be a blister-type container. In one embodiment of the invention the pharmaceutical product or container closure system can be realized by an overpouch which has an intransparent first foil and a transparent second foil which are weldable or welded together for carrying the primary container comprising a pharmaceutical solution.

Preferably the intransparent first foil and the transparent second foil are provided by a multilayer film. Preferably the intransparent first foil of the overpouch has an outer layer of a polyester layer or of a polypropylene layer and/or an inner layer of an intransparent polypropylene layer to provide the inner surface as the background. In one embodiment a metallic layer, preferably an aluminum layer is located between the inner layer and the outer layer.

Preferably the transparent second foil of the overpouch has an outer layer of polyester, preferably of polyethylene terephthalate, and an inner layer of polypropylene. In one embodiment an inorganic oxide layer is located between the inner layer and the outer layer.

The inorganic oxide layer of the transparent second multilayer foil avoids the permeability of oxygen and water vapor. In particular by this inorganic oxide layer the object of the invention is attained that the labels of the primary container are readable while it is overwrapped and sealed by the sealed overpouch and while the impermeability of the overpouch for oxygen is still warranted. It is neither necessary to get the primary container out of the overpouch nor to reprint the at least one label on the overpouch to get the information of the label of the primary container. Furthermore, the inorganic oxide layer of the transparent second foil inhibits water vapor transmission and protects the primary container from any other environmental impact.

In a further embodiment of the invention the inorganic oxide layer of the transparent second foil is made of an oxide of aluminum and/or silicon, especially of an aluminum oxide of the form $AlO_x$. This oxide could be deposited directly on the surface of the polyethylene terephthalate layer of the second multi-layer foil so that no additional glue is necessary to get the oxide connected to the polyethylene terephthalate layer of the second foil of the overpouch. In case of aluminium foils for such an overpouch it is a multi-layer film preferably with a composition of more than 60% polypropylene, more than 10% aluminium, less than 20% polyester and less than 5% of a glue system (percentage by weight).

To simplify the manufacturing process of overwrapping and sealing the primary container within the overpouch the first and/or the second multi-layer foil are/is deepdrawable. By this embodiment it is possible that the form of the overpouch is adapted to the form of the primary container during the manufacturing process of a pharmaceutical product or container closure system consisting of the overpouch, the primary container and the pharmaceutical solution within the primary container.

The exemplary features of the layers of the intransparent first foil are as following:

The polyester layer of the intransparent first foil of the overpouch consists of or comprises polyethylene terephthalate and/or the polypropylene layer of the intransparent first foil of the overpouch consists of or comprises oriented polypropylene.

This polyester layer and/or this polypropylene layer and/or the metallic layer of the intransparent foil have a thickness between 5 μm and 50 μm, preferably 12 μm and 25 μm.

The intransparent polypropylene layer of the intransparent first foil has a thickness between 50 μm and 150 μm, preferably 75 μm and 85 μm.

While the metallic layer, preferably aluminum layer, is responsible for the protection of oxygen, water vapor and light permeability of the intransparent foil of the overpouch, the intransparent polypropylene layer with the preferred thickness between 75 μm and 85 μm is responsible for a good and sufficient stiffness and mechanical stability and concomitantly being also a good water vapor and oxygen barrier of the overpouch.

To easily recognize labels and/or barcodes printed on the primary container, the intransparent polypropylene layer of the intransparent first foil is colored white in one embodiment. On such a white background labels as barcodes printed on the primary container are visible very well since they are usually printed with black or dark colored ink which provides a very good contrast to the white background. But it is still possible within the invention that the intransparent polypropylene layer of the intransparent first foil is colored dark, preferably black, while the labels are printed in bright color, preferably in white, on the primary container. In both cases a good contrast of the label of the primary container on the background of the intransparent foil of the overpouch is given.

The exemplary features of the layers of the transparent second foil are as following:

In one embodiment the polyester layer, preferably a polyethylene terephthalate layer, of the transparent second foil of the overpouch has a thickness between 5 μm and 50 μm, preferably 12 μm and 25 μm.

In one embodiment the polypropylene layer of the transparent second foil of the overpouch has a thickness between 50 μm and 150 μm, preferably 75 μm and 85 μm.

Especially the polypropylene layer with the mentioned thickness raises the stiffness and mechanical stability of the overpouch once more. If the stiffness and/or mechanical stability has to be particular high between the polyethylene terephthalate layer and the polypropylene layer of the transparent first foil of the overpouch, an additional polyester layer, preferably polyethylene terephthalate layer, can be located within these two layers. This layer can have a thickness between 5 μm and 50 μm, preferably 12 μm and 25 μm.

On the outer wall of the transparent first foil of the overpouch the polyester layer, preferably the polyethylene terephthalate layer, is sealed with a heat sealable coating in a further embodiment. Overheating of the pharmaceutical liquid within the primary container during storage can be prevented.

Since the intransparent first foil and/or the transparent second foil of the overpouch is/are preferably provided by single layers, theses single layers are laminated together by means of glue.

The primary container of the inventive pharmaceutical product or container closure system is preferable a fully transparent polyolefin bag, holding the (transparent) solution. The entire pharmaceutical product or container closure system can be subjected to heat sterilization. The polypropylene layer of the intransparent first foil of the overpouch is white coloured. This assembly and especially the white background make the label printed directly with dark, respectively black, colour onto the primary container readable through the transparent second multi-layer foil of the overpouch. Hence, the second label printed usually on the overpouch becomes redundant. Furthermore, visual inspection can be performed more accurate on the white background. Therefore, only one label can be used for a double packed pharmaceutical liquid but still all information inevitably printed on the primary bag is disclosed and readable with the naked eye or with a machine, without a second label printed or glued on the overpouch. The human and/or machine readability of the label on the white background is significantly better as on the usually silver or dark background, for instance provided by an aluminium surface. In addition any potential change in quality can be detected without destruction of the overpouch.

Especially for transparent primary containers which are filled with transparent pharmaceutical solutions like a paracetamol solution the containers can be furthermore inspected better with respect to quality parameters like colour change or visible particles. A colour change, often a sign of degradation of the finished product, is well detectable on the white background with the naked eyes or a machine. The same can be stated for visible particles. Both parameters can be tested without destruction of the overpouch, hence removal of the oxygen protecting shell.

The preferred method of sterilization of the pharmaceutical product or container closure system is heat sterilization. In addition to the oxygen impermeable overpouch, an oxygen absorber is added between the primary container and the overpouch as a protecting agent against oxidation of the active pharmaceutical ingredient. The oxygen absorber, for example, could be positioned between two ports of the primary container, so that the readability of the label is not jeopardized. One port could be used for the infusion of the content of the primary bag into the patient. Another port, for example, could be used for injection (addition) of other compatible drugs. The primary container film could be a flexible multi-layer film made of polyolefine and has good chemical resistance, good welding characteristics, good water vapor barrier and is heat sterilisable.

If the entered oxygen in the overpouch cannot be bound anymore by the oxygen absorber or no absorber is present in the sealed overpouch within the sealed overpouch, an oxygen indicator can be present, which is preferable located on the outside of the primary container outside the area of the label of the primary container. Such an oxygen indicator changes its color if free oxygen is present so that it is easily recognizable if oxygen has entered the sealed overpouch and could not be bound by an oxygen absorber. This is important since the primary container comprises pharmaceutical solutions, which potentially contain an oxygen sensitive active ingredient.

The first and second multilayer foils of the overpouch exhibit an oxygen permeability of less than 3 $cm^3/(m^2*day*bar)$, in accordance to ISO standard 15105-2, at 23° C. and 50% r.h., whereby average values are measured around 0.4-0.5 $cm3/(m^2*day*bar)$. The water vapor permeation is specified with <1 $g/(m^2*day)$ in accordance to ISO standards 15106-3 at 23° C. and 85% r.h., whereby values of approximately 0.4 $g/(m^2*day)$ are obtained. The foils were tested at conditions of 23° C./85% r.h after subjecting the foils to an autoclave cycle of 121° C./30 minutes.

Further goals, advantages, features and applications of the invention arise from the following description of embodiments of the invention on the basis of the figures. The features of the different embodiments are able to be combined with one another. Thereby all features described and all features shown in the figures alone or in arbitrary reasonable combination provide the subject matter of the invention independent of their conclusion in the claims or their dependency.

Subsequently, preferred but exemplary embodiments of the invention are described in more detail with regard to the figures.

DETAILED DESCRIPTION OF THE INVENTION

Figure 1:
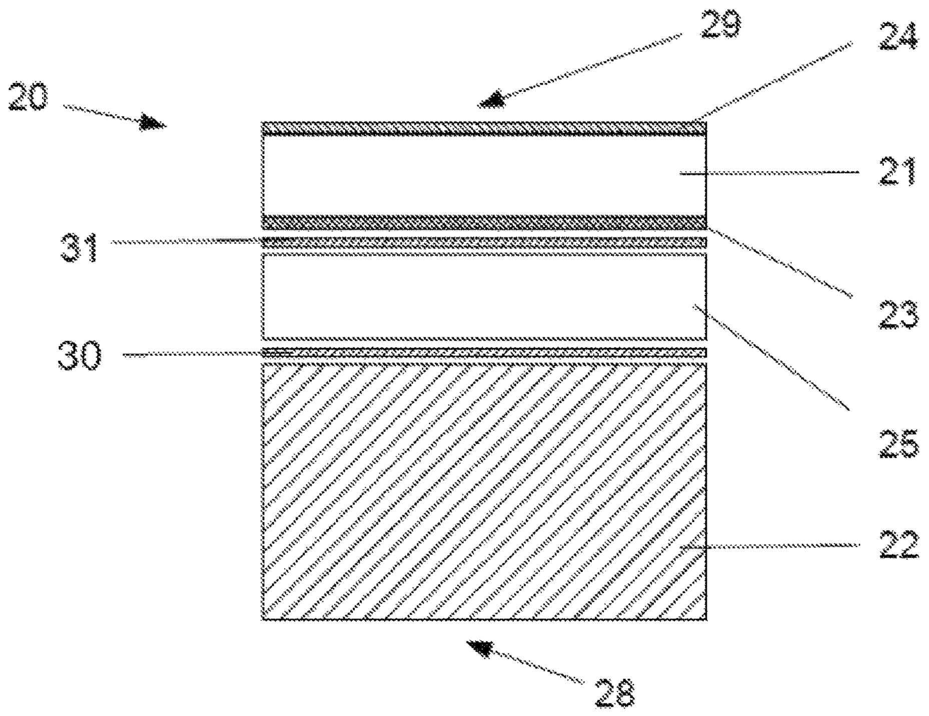
FIG. 1: an exploded view of a schematically sectional view of one embodiment of a transparent foil of an overpouch of an inventive pharmaceutical product or closure system.
Figure 2:
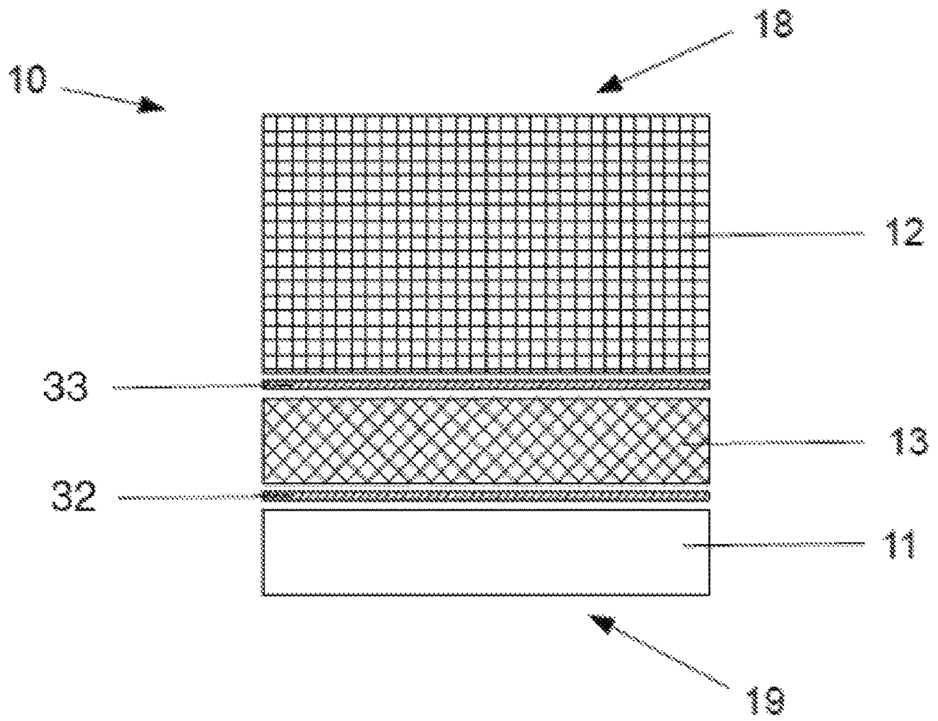
FIG. 2: an exploded view of a schematically sectional view of one embodiment of an intransparent foil of an overpouch inventive of an inventive pharmaceutical product or closure system.

In the FIGS. 1 and 2 a transparent foil 20 and an intransparent foil 10 of one embodiment of an overpouch 1 of an inventive pharmaceutical product or container closure system are shown in an exploded view of a schematically sectional view. The sectional composition of the transparent foil 20 and the intransparent foil 10 of the overpouch 1 are clearly visible.

The transparent second foil 20 of the overpouch 1 which is transparent is shown in FIG. 1. In one embodiment the transparent foil 20 is not deepdrawable. To the outside of the overpouch 1 the transparent foil 20 is delimited by a polyethylene terephthalate layer 21 which is used as an outer wall 29 of the transparent foil 20. In the shown embodiment the polyethylene terephthalate layer 21 is coated on the outside with a heat sealable coating 24 which inhibits heat transmission into the overpouch 1 and into a primary container 2 of a pharmaceutical product or container closure system, respectively, when the filled primary container 2 is sealed by the overpouch 1 and, for example, stored in a storage.

On the inner side of the polyethylene terephthalate layer 21 an inorganic oxide layer 23, in particular an aluminum oxide layer, is preferably directly deposited. This oxide layer 23 builds a barrier for oxygen, water vapor and other gases within the transparent foil 20.

The polyethylene terephthalate layer 21, the heat sealable coating 24 and the inorganic oxide layer 25 form a layer assembly having a thickness of about 10 μm to 15 μm, preferably 12 μm. This layer assembly is bonded to an additional polyethylene terephthalate layer 25, preferably having a thickness between 12 μm and 25 μm, by means of glue 31. This additional polyethylene terephthalate layer 25 is furthermore bonded to a transparent polypropylene layer 22, preferably having a thickness between 75 μm and 85 μm, by means of glue 30. The main function of the additional polyethylene terephthalate layer 25 and the polypropylene layer 22 is in particular to enhance the stiffness and the mechanical stability of the transparent foil 20, the overpouch 1 and the pharmaceutical product or container closure system. Furthermore, the transparent polypropylene layer 22 forms the inner wall 28 of the second multi-layer foil 20 of the overpouch 1. Preferably all layers of the transparent foil 20 are transparent or essentially transparent.

If a primary container 2 which is filled with a pharmaceutical solution 3 is sealed with an overpouch 1 containing a transparent foil 20 as the above described second multi-layer foil 20, it is possible to look through the transparent foil 20 into the interior of the overpouch 1 and to recognize label 4, for instance in form of barcodes 4*a* arranged on the primary container, while gas permeation through transparent foil 20 is inhibited essentially by the inorganic oxide layer 23. So it is possible to read all information labeled on the primary container) without destroying the overpouch 1 and the protection for the primary container 1 and the pharmaceutical solution therein, respectively.

The first multi-layer foil 10 of the overpouch 1 which is intransparent is shown in FIG. 2. In a preferred embodiment the intransparent first multi-layer foil 10 is deepdrawable. To the outside of the overpouch 1, the intransparent foil 10 is delimited in this embodiment by a polyester layer 11 which is used as an outer wall 19 of the intransparent foil 10. In a specific embodiment, the polyester layer 11 is formed out of polyethylene terephthalate, preferably having a thickness between 12 μm and 25 μm. In a further embodiment the intransparent foil 10 is delimited by a polypropylene layer 11 which is used as an outer wall 19 of the intransparent foil 10. In a specific embodiment, the polypropylene layer 11 is formed out of oriented polypropylene, preferably having a thickness between 12 μm and 25 μm.

This layer 11 is bonded to an aluminum layer 13, preferably having a thickness between 12 μm and 25 μm, by means of glue 32. That aluminum layer 13 builds a barrier for oxygen, water vapor and other gases within the intransparent foil 10.

Furthermore, this aluminum layer 13 is bonded to a polypropylene layer 12, preferably having a thickness between 75 μm and 85 μm, by means of glue 33. One function of this polypropylene layer 12 is to enhance the stiffness and the mechanical stability of the intransparent foil 10, the overpouch 1 and the pharmaceutical product or container closure system. The main function of this polypropylene layer 12 is hidden in its white color. Because of the white coloring of the polypropylene layer 12 labels 4 as barcodes 4*a* which are printed in black or generally in dark color on transparent primary containers 2 which are filled with a preferable transparent pharmaceutical solutions 3 are very good readable by humans and machines. The black or dark printing on the primary container gives a good contrast to the white background.

Furthermore, because of the aluminum layer 13 of the intransparent foil 10 and the inorganic oxide layer 23 of the second multi-layer foil 20, a good protection against oxygen, water vapor and other gases is provided for pharmaceutical solutions 3 within a primary container 2 when the overpouch 1 with the described transparent foil 20 and the intransparent foil 10 are used for overwrapping and sealing.

Figure 3:
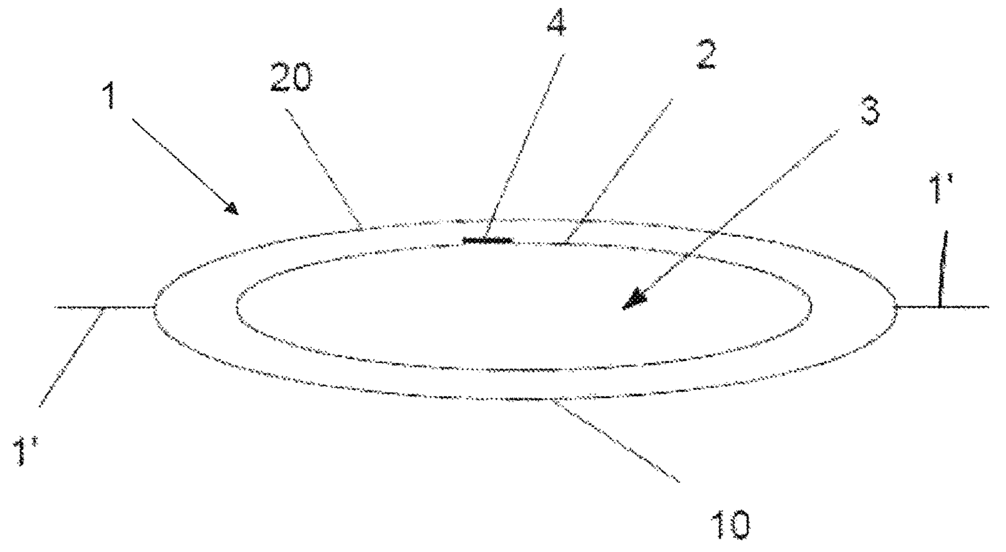
FIG. 3: one embodiment of an inventive pharmaceutical product or container closure system in a schematically sectional view.

FIG. 3 shows one embodiment of an inventive pharmaceutical product or container closure system in a schematically sectional view wherein a primary container 2 with a pharmaceutical solution is overwrapped and sealed by an inventive overpouch 1. The filled primary container 2 is securely held within the overpouch 1 and therefore, the pharmaceutical solution 3 is protected against oxygen, water vapor and other gases. On the primary container 2 beneath the transparent foil 20 of the overpouch 1 a label 4 is printed. The label 4 can be embodied as and/or can comprise a 1-dimensional or 2-dimensional barcode or data matrix. As clearly shown in FIG. 3, the overpouch 1 is formed out of the intransparent foil 10 and the transparent foil 20 which are welded together in a welding area 1' in a boundary area of the overpouch 1.

If a machine or a human being wants to read the label 4 of the primary container 2 it is necessary that electromagnetic radiation has to fall onto the pharmaceutical product or container closure system. Since human beings can see electromagnetic radiation in the visible range between 350 nm to 800 nm the label 4 of the primary container 2 has a refection property of $R_L$ while the intransparent foil 20 of the overpouch 1 has a refection property of $R_F$ in that range. For instance in this embodiment the following parameters could be used: $R_F \leq 0.05$ while $R_L \geq 0.80$. The difference of the reflected radiation in the visible range of electromagnetic radiation between 350 nm to 800 nm gives a good contrast of the at least one label of the primary container on the background of the intransparent foil of the overpouch since a symbol contrast SC which is defined by the absolute value of the difference of $R_F$ and $R_L$ has a high value of at least 0.75. Therefore the contrast of the label 4 of the primary container 2 is very good on the background of the intransparent foil 20 of the overpouch so that the label can be read easily by human beings as well as by machines through the transparent foil 10 of the overpouch.

The reflection of the transparent foil 20 of the overpouch 1 and the transparent primary container 2 and the transparent pharmaceutical solution 3 do not essentially contribute and can therefore be neglected even if the radiation reflected by intransparent foil 10 of the overpouch 1 is running twice through it.

Figure 4:
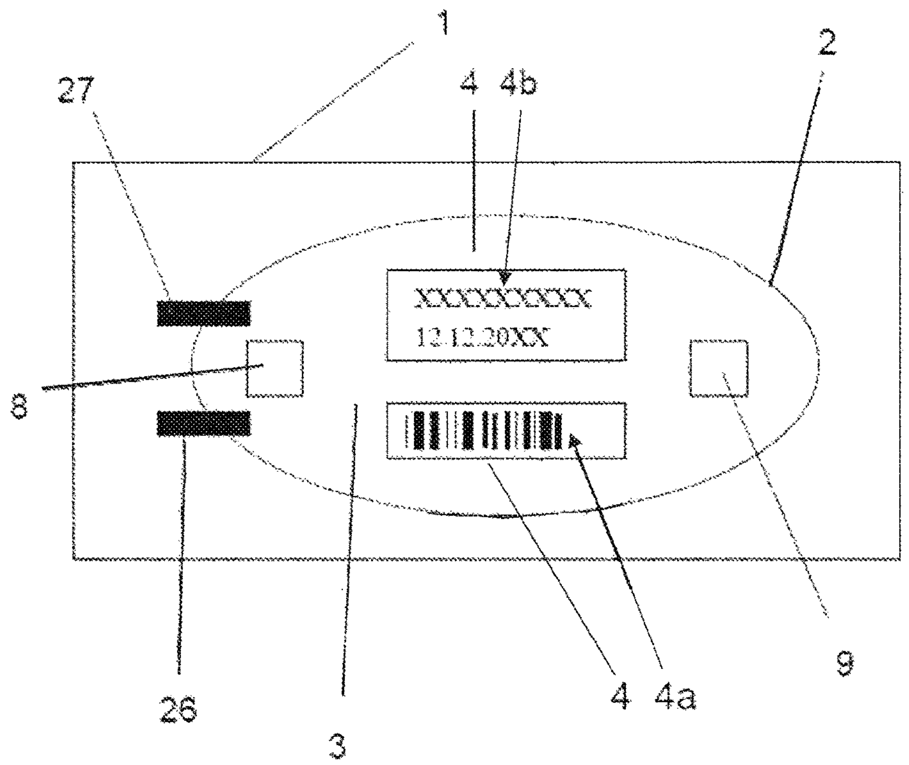
FIG. 4: the inventive pharmaceutical product or container closure system of FIG. 3 in a view from above through the transparent foil of an overpouch of the inventive pharmaceutical product or container closure system.

FIG. 4 shows one embodiment of an inventive pharmaceutical product or container closure system in a view from above through the transparent second multi-layer 20 foil of an overpouch 1 of the pharmaceutical product or container closure system. In particular, this illustration makes the goal of the invention very clear.

The primary container 2 is filled with a pharmaceutical solution 3 and printed with a label 4, 4*b*, 4*c* which contains for instance information of the content 6 and information of the use 7 of the primary container. By reading this information 6 and 7 it is possible that humans can be informed directly about the use and the content. Furthermore, a label 4 with a barcode 4*a* was printed on the primary container 2 so that all necessary information is stored therein and can be read by a machine which can deliver this information to a data management system, especially a healthcare, patient and/or drug management and administration system. The labels 4 and the barcode 4*a* are printed preferably with black color, for instance ink, on the transparent primary container 2 so that this black ink builds up a very good contrast to the white intransparent polypropylene layer 12 of the first multi-layer foil 10 of the overpouch 1 which is visible because of the transparent foil 20 of the overpouch and the different reflections $R_F$ of the intransparent foil 10 of the overpouch 1 and $R_L$ of the labels 4, 4*a*, 4*b* and 4*c*.

Especially when the pharmaceutical solution 3 within the primary container 2 is transparent, too, it is even possible to inspect the pharmaceutical solution 3 optically by humans or by machines. On the white background contaminations especially in form of particles or turbidities or color changing have a good visibility and are good indicators or signs of degeneration of the pharmaceutical solution 3 within the primary container 2.

Additionally, ports 26, 27, oxygen absorber 8 and oxygen indicator 9 are illustrated in FIG. 4. The oxygen absorber 8 is located on the surface of the primary container 2 in direction to the overpouch 1. This oxygen absorber 8 is located between two ports 26 and 27 of the primary container so that it does not block the labels 4 or the barcode 4*a* so that they are still visible. One port 26 can be used for infusion of a pharmaceutical solution 3 while the other port 27 can be used for adding additional pharmaceuticals or drugs into the pharmaceutical solution after destroying the overpouch 1 and before infusing the pharmaceutical solution into a patient.

Although the overpouch 1 should be gas tight, it is possible that leaks occur through which, in particular, oxygen can enter the overpouch and contaminate the pharmaceutical solution 3 within the primary container 2. To detect such an entry of oxygen into the sealed overpouch an oxygen indicator 9 is also located on the surface of the primary container 2 in a way that neither the labels 4 nor the barcode 4*a* are blocked. Such an oxygen indicator 9 changes its color if oxygen is present in the sealed overpouch 1 so that an oxygen entry easily can be determined.

As already mentioned before, FIGS. 3 and 4 illustrate an embodiment where the label 4 is provided by black color on the transparent primary container 2. The inner surface 18 of the intransparent first foil 10 is provided by white color, preferably a white colored layer.

Figure 5:
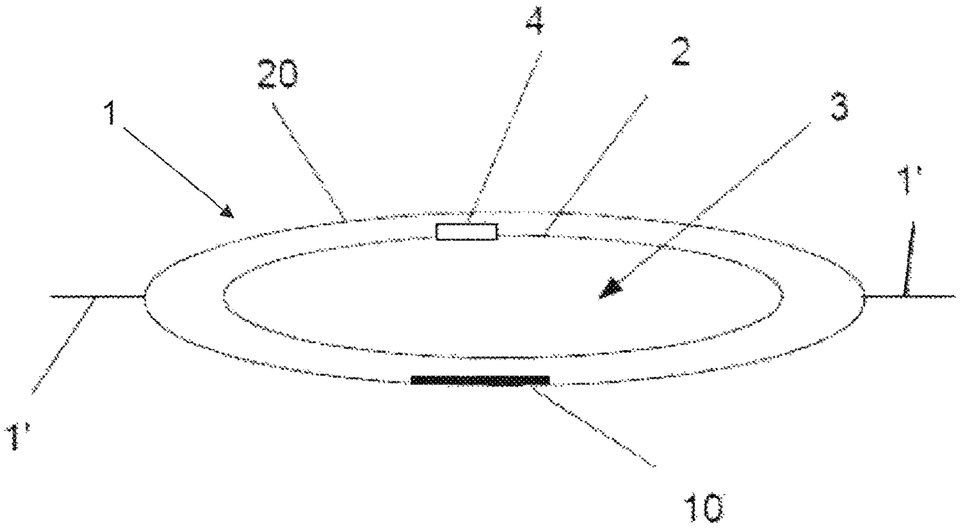
FIG. 5: one further embodiment of an inventive pharmaceutical product or container closure system in a schematically sectional view
Figure 6:
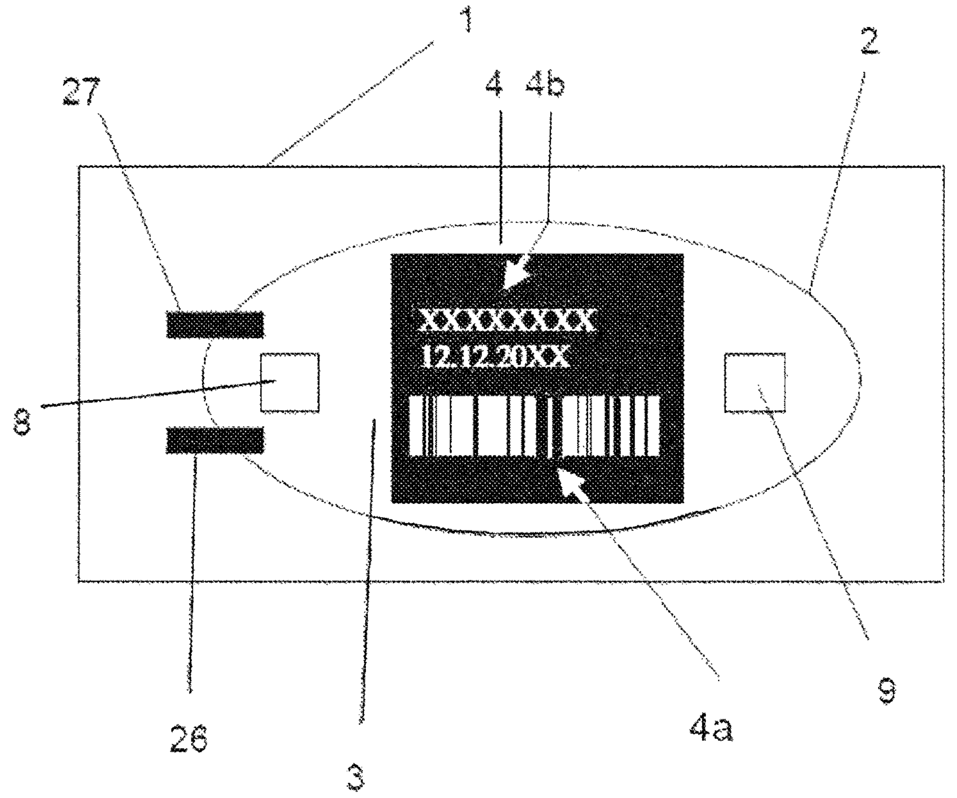
FIG. 6: the inventive pharmaceutical product or container closure system of FIG. 5 in a view from above through the transparent foil of an overpouch of the inventive pharmaceutical product or container closure system.

Finally, FIGS. 5 and 6 illustrate a further embodiment of an inventive pharmaceutical product or container closure system. In contrast to FIGS. 3 and 4 the label 4 is provided by white color on the transparent primary container 2. The inner surface 18 of the intransparent first foil 10 is provided by black color, preferably a black colored layer. In addition, it is illustrated that only a part of the inner surface 18 of the intransparent first foil 10 is provided with the black color. The intransparent area is located below or covered by the area of the primary container 2 in which the label 4 is located.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, features of the above described specific embodiments can be combined with one another. Further, features described in the summary of the invention can be combined with one another. Furthermore, features of the above described specific embodiments and features described in the summary of the invention can be combined with one another.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Other than in the operating examples, or where otherwise indicated, all numbers expressing quantities of ingredients, reaction conditions, and so forth used in the specification and claims are to be understood as being modified in all instances by the term "about."

Accordingly, unless indicated to the contrary, the numerical parameters set forth herein are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

REFERENCE SIGNS

1 overpouch
1' welded area of the overpouch
2 primary container
3 pharmaceutical solution
4 label
4*a* barcode
4*b* label with information of the content of the primary container
4*c* label with information of the use of the primary container
6 information of the content of the primary container
7 information of the use of the primary container
8 oxygen absorber
9 oxygen indicator
10 intransparent foil
11 polyester layer or polypropylene layer
12 intransparent colored polypropylene layer
13 aluminum layer
18 inner wall or surface
19 outer wall or surface
20 transparent foil
21 polyethylene terephthalate layer
22 polypropylene layer
23 inorganic oxide layer
24 heat sealable coating
25 polyethylene terephthalate layer
26 port
27 port
28 inner wall
29 outer wall
30 glue
31 glue
32 glue
33 glue
$R_F$ reflection of the intransparent foil 10 or its inner surface 18
$R_L$ reflection of the label 4, 4*a*, 4*b* and 4*c*

The invention claimed is:

1. A pharmaceutical product comprising an overpouch with an intransparent first foil and a transparent second foil, wherein the intransparent first foil comprises a colored polymeric layer, and a transparent primary container containing a pharmaceutical formulation, wherein the transparent primary container is packed within the overpouch and labeled with at least one label comprising a barcode or a data matrix and wherein the label is machine-readable through the transparent second foil of the overpouch, and wherein the at least one label has a reflection $R_L$ for light in the range of 350 nm to 800 nm and an inner surface of the intransparent first foil of the overpouch has a reflection $R_F$ for light in the direction of the primary container in the range of 350 nm to 800 nm, wherein $R_L \neq R_F$, and wherein $0.5 \times R_F \geq R_L$ and $R_F \geq 0.5$.

2. The pharmaceutical product according to claim 1, wherein the at least one label acts as light absorbing segment and the overpouch acts as a light reflecting background.

3. The pharmaceutical product according to claim 1, wherein the label is a dark color, and the inner surface of the intransparent first foil of the overpouch is a light color, or the label is a light color, and the inner surface of the intransparent first foil of the overpouch is a dark color.

4. The pharmaceutical product according to claim 1, wherein the label is imprinted on the outer side of the transparent primary container facing the transparent second foil of the overpouch, and the inner surface of the intransparent first foil of the overpouch comprises a colored polymeric layer.

5. The pharmaceutical product according to claim 1, wherein the label contains information related to the content of the primary container.

6. The pharmaceutical product according to claim 1, comprising a symbol contrast (SC) wherein $SC=|R_F-R_L|\geq 0.5$.

7. The pharmaceutical product according to claim 1, wherein $R_F \geq 0.9$, and $R_L \leq 0.1$.

8. The pharmaceutical product according to claim 1, wherein the intransparent first foil of the overpouch is a multilayer-foil having an outer layer and an inner layer providing the inner surface.

9. The pharmaceutical product according to claim 8, comprising a metallic layer located between the outer layer and the inner layer.

10. The pharmaceutical product according to claim 9, wherein the outer layer is a polyester layer or a polypropylene layer, the inner layer is an intransparent polypropylene layer, and the metallic layer is an aluminum layer.

11. The pharmaceutical product according to claim 10, wherein the polyester layer comprises polyethylene terephthalate or the polypropylene layer comprises an oriented polypropylene layer.

12. The pharmaceutical product according to claim 10, wherein the polyester layer, the polypropylene layer and the metallic layer have a thickness between 5 μm and 50 μm and the intransparent polypropylene layer has a thickness between 50 μm and 150 μm.

13. The pharmaceutical product according to claim 1, wherein the transparent second foil of the overpouch is a multilayer foil having an outer layer and an inner layer.

14. The pharmaceutical product according to claim 13, comprising an inorganic oxide layer located between the outer layer and the inner layer.

15. The pharmaceutical product according to claim 14, wherein the inorganic oxide layer comprises an oxide of aluminum or silicon.

16. The pharmaceutical product according to claim 13, wherein the outer layer is a first polyester layer and the inner layer is a polypropylene layer.

17. The pharmaceutical product according to claim 16, wherein the polyester layer is sealed on the outside of the overpouch with a heat sealable coating.

18. The pharmaceutical product according to claim 16, wherein the polyester layer has a thickness between 5 μm and 50 μm and the polypropylene layer has a thickness between 50 μm and 150 μm.

19. The pharmaceutical product according to claim 16, comprising a second polyester layer having a thickness between 5 μm and 50 μm located between the first polyester layer and the polypropylene layer.

20. The pharmaceutical product according to claim 19, wherein the first polyester layer and the second polyester layer comprise polyethylene terephthalate.

21. The pharmaceutical product according to claim 1, further comprising an oxygen absorber or an oxygen indicator.

22. The pharmaceutical product according to claim 1, wherein the intransparent first foil is deepdrawable.

23. A container closure system comprising an overpouch with an intransparent first foil and a transparent second foil, wherein the intransparent first foil comprises a colored polymeric layer, and a transparent primary container for holding a liquid, wherein the transparent primary container is packed within the overpouch and labeled with at least one label comprising a barcode or a data matrix and wherein the label is machine-readable through the transparent second foil of the overpouch and wherein the at least one label has a reflection $R_L$ for light in the range of about 350 nm to about 800 nm and an inner surface of the intransparent first foil of the overpouch has a reflection $R_F$ for light in the direction of the primary container in the range of 350 nm to 800 nm, wherein $R_L \neq R_F$, and wherein $0.5 \times R_F \geq R_L$ and $R_F \geq 0.5$.

24. The container closure system according to claim 23, wherein the at least one label acts as light absorbing segment and the overpouch acts as a light reflecting background, and wherein $R_F > R_L$.

25. A pharmaceutical product comprising an overpouch with an intransparent first foil and a transparent second foil, wherein the intransparent first foil comprises a colored polymeric layer, a transparent primary container containing a pharmaceutical formulation, wherein the transparent primary container is packed within the overpouch and labeled with at least one label comprising a barcode or a data matrix and wherein the label is machine-readable through the transparent second foil of the overpouch and wherein the at least one label has a reflection $R_L$ for light and an inner surface of the intransparent first foil of the overpouch has a reflection $R_F$ for light in the direction of the primary container, wherein $0.5 \times R_F \geq R_L$ and $R_F \geq 0.5$.

* * * * *